US00PP25793P3

(12) United States Plant Patent
Bradford

(10) Patent No.: US PP25,793 P3
(45) Date of Patent: Aug. 11, 2015

(54) PEACH TREE NAMED 'SUMMER PRINCESS'

(50) Latin Name: *Prunus persica*
Varietal Denomination: Summer Princess

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 78 days.

(21) Appl. No.: 13/998,861

(22) Filed: Dec. 16, 2013

(65) Prior Publication Data

US 2015/0173278 P1 Jun. 18, 2015

(51) Int. Cl.
*A01H 5/08* (2006.01)

(52) U.S. Cl.
USPC ..... Plt./197

(58) Field of Classification Search
USPC ..... Plt./197
CPC ..... A01H 5/0868; A01H 5/0837
See application file for complete search history.

(56) References Cited

U.S. PATENT DOCUMENTS

PP10,926 P 6/1999 Bradford et al.

OTHER PUBLICATIONS

U.S. Appl. No. 13/694,608, filed Dec. 13, 2012, Bradford.

*Primary Examiner* — Kent L Bell

(57) ABSTRACT

The present invention relates to a new and distinct variety of peach tree, *Prunus persica*, broadly characterized by a large size, vigorous, hardy, self-fertile, productive and regular bearing tree. The variety blooms during the mid to late season and requires about 600 chilling hours. The fruit matures under the ecological conditions described in late August, with first picking on Aug. 25, 2013. The fruit is uniform, very large in size, acidic with traditional peach flavor, nearly globose in shape, clingstone in type, firm in texture, yellow in flesh color, virtually full red in skin color, and has a bitter tasting kernel.

1 Drawing Sheet

Botanical classification: *Prunus persica.*
Variety denomination: 'SUMMER PRINCESS'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of peach tree, which has been denominated varietally as 'Summer Princess'.

In 2003 I made a first generation hybridization using 'August Pearl' (U.S. Plant Pat. No. 10,926) nectarine as the selected seed parent and an unnamed yellow flesh peach as the selected pollen parent. The fruit of this cross was gathered that summer, and the seeds were removed, cracked, stratified, germinated, and grown as seedlings on their own root in my greenhouse facility. Upon reaching dormancy I transplanted them to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

While the present variety is similar to its seed parent, 'August Pearl' nectarine, in several aspects, such as producing fruit that is mostly red in skin color, clingstone in type, and firm in texture, but it is quite distinguished from it by being a yellow flesh peach instead of white flesh nectarine.

The present variety is most similar to Red Princess (U.S. Plant Pat. No. 24,729) peach by requiring about 600 chilling hours, by blooming in the mid to late season, by being self-fruitful, by having large blossoms, and by producing yellow flesh clingstone peaches that are firm, nearly full red in skin color, globose in shape, and a good tasting flavor, but is distinguished therefrom by having a larger and more vigorous tree, by having globose instead of reniform glands, and by producing fruit that is somewhat larger in size, that has a bitter kernel instead of sweet, and that matures about seventy days later.

SUMMARY OF VARIETY

In summary, the present peach variety is characterized by a large size, vigorous, hardy, self-fertile, productive and regular bearing tree. The variety blooms during the mid to late season and requires about 600 chilling hours. The fruit matures under the ecological conditions described in late August, with first picking on Aug. 25, 2013. The fruit is uniform, very large in size, acidic with traditional peach flavor, nearly globose in shape, clingstone in type, firm in texture, yellow in flesh color, virtually full red in skin color, and has a bitter tasting kernel.

DRAWING

The accompanying photograph consists of four whole fruits positioned to display the characteristics of the skin color and form, one sliced fruit to reveal the flesh and stone, two insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Sep. 5, 2013, on the original tree during its tenth growing season. The blossom and flower descriptions were made the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: August Pearl (U.S. Plant Pat. No. 10,926) nectarine.

Pollen parent: Unnamed peach.

TREE

Size: Large, reaching and maintaining a height of 14' [4.27 m.] and a spread of 13' [3.96 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase form.

Hardiness: Hardy with respect to central California winters.

Chilling requirement: About 600 hours.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Trunk:

- *Size*.—Medium, reaching a maximum diameter of 7" [177.8 mm.] after the tenth growing season.
- *Texture*.—Medium, shaggy.
- *Bark color*.—A Light grayish brown [60. l.gy.Br] and Grayish brown [61. gy.Br] variegation with Light brown [57. l.Br] crevices present.
- *Lenticels*.—Approximate Number Per Square Inch: 10. Color: Grayish yellowish brown [80. gy.yBr]. Size: ⅛" [3.2 mm.] to ¼" [6.4 mm.]. Shape: Eye-shaped, elongated.

Branches:

- *Size*.—Diameter of limb is 3" [76.2 mm.] measured 12" above the crotch, 1⅜" [34.9 mm.] measured 12" above the first fork.
- *Texture*.—Smooth on first and second year wood, increasing roughness with age.
- *Color*.—1st Year Wood Topside: Grayish red [19. gy.R]. 1st Year Wood Underside: Brilliant yellow green [116. brill.YG]. 2nd Year Wood: A Moderate yellowish brown [77. m.yBr] and Grayish brown [61. gy.Br] variegation.
- *Lenticels*.—Number Per Square Inch: About 60 on second year wood. Color: Light yellowish brown [76. l.yBr]. Average Size: 1/16" [1.6 mm.]. Shape: Elongated, eye-shaped.

Leaves:

- *Size*.—Large. Average Length: 6" [152.4 mm.]. Average Width: 1⅝" [41.3 mm.].
- *Arrangement*.—Alternate.
- *Thickness*.—Medium.
- *Form*.—Elliptical.
- *Apex*.—Acuminate.
- *Base*.—Rounded to slightly acute.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: 7/16" [11.1 mm.]. Average Thickness: 1/16" [1.6 mm.]. Color: Strong yellow green [117. s.YG].
- *Stipules*.—Number: 2 per leaf, up to 6 per growing tip. Average Length: 5/16" [7.9 mm.]. Color: Moderate yellow green [120. m.YG] becoming Dark grayish brown [62. d.gy.Br] with age.
- *Glands*.—Number: Mostly 2 to 6 per leaf. Position: Alternately positioned on the petiole and base of blade. Size: Small. Form: Globose. Color: Moderate yellow green [120. m.YG] becoming Grayish brown [61. gy.Br] in the center with age.
- *Leaf buds*.—Pointed, medium.

Flower buds:

- *Hardiness*.—Hardy, with respect to central California winters.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Light purplish pink [249. l.pPk].

Flowers: Perfect, complete, perigynous, usually a single pistil, about thirty stamens, five sepal and petal locations alternately positioned.

- *Type*.—Showy, large.
- *Average flower diameter*.—1 15/16" [49.2 mm.].
- *Number of petals*.—Mostly five, extra petal fragments or double blossoms are occasionally observed.
- *Petal shape*.—Circular to oval.
- *Petal margin*.—Entire, quite wavy.
- *Average petal diameter*.—¾" [19.1 mm.].
- *Average petal length*.—¾" [19.1 mm.].
- *Petal apex*.—Rounded.
- *Petal base*.—Rounded to somewhat truncate.
- *Petal color*.—Light pink [4. l.Pk] toward the apex, Moderate pink [5. m.Pk] toward the base on both sides.
- *Anther color*.—Moderate reddish orange [37. m.rO] over a Light yellow [86. l.Y] center at bloom onset.
- *Stigma color*.—Pale greenish yellow [104. p.gY].

*Sepal color*.—Dark purplish red [259. d.pR] on the outer surface.
*Sepal length*.—¼" [6.4 mm.].
*Sepal width*.—3/16" [4.8 mm.].
*Sepal apex*.—Rounded to elliptical to match the sepal length and width.
*Sepal margin*.—Fairly smooth.
*Average pistil length*.—⅝" [15.9 mm.].
*Average stamen length*.—½" [12.7 mm.].
*Fragrance*.—Moderate.
*Blooming period*.—Medium to late, four days before 'Diamond Princess' (U.S. Plant Pat. No. 7,066) peach.
*Onset of bloom*.—One percent on Mar. 8, 2013.
*Date of full bloom*.—Mar. 15, 2013.
*Duration of bloom*.—One to two weeks, dependent on ambient temperature.
*Number per cluster*.—1 to 3 with single flowers most common.

FRUIT

Maturity when described: Firm ripe, Sep. 5, 2013.
Date of first picking: Aug. 25, 2013.
Date of last picking: Sep. 10, 2013.
Size: Uniform, large.
*Average diameter axially*.—3¼" [82.6 mm.].
*Average diameter across suture plane*.—3½" [88.9 mm.].
*Average diameter across cheek plane*.—3½" [88.9 mm.].
*Typical weight*.—12.9 ounces [366 grams].
Form: Uniform, globose, symmetrical.
*Longitudinal section form*.—Round to slightly oblate.
*Axial view*.—Round.
Suture: Extends from the base to somewhat beyond the pistil point.
*Near the base*.—A shallow groove.
*Along the side*.—A shallow trough with some stitching.
*Near the apex*.—A sharp groove.
Ventral surface: Rounded, lipped slightly toward the apex.
Lips: Slightly unequal.
Cavity: Flaring, elongated in the suture plane, suture showing on one side, Brilliant yellow [83. brill.Y] stem markings typical.
*Depth*.—1½" [38.1 mm.].
*Breadth*.—13/16" [20.6 mm.].
Base: Truncate.
Apex: Rounded.
Pistil point: Some apical and some oblique, typically ⅛" [3.2 mm.] in length, sometimes depressed within the suture.
Stem: Medium.
*Average length*.—⅜" [9.5 mm.].
*Average width*.—3/16" [4.8 mm.].
Skin:
*Thickness*.—Medium.
*Surface*.—Pubescent.
*Tenacity*.—Tenacious to the flesh.
*Astringency*.—Slight.
*Tendency to crack*.—None observed in dry season.
*Color*.—Very deep red [14. v.deep R] smoothly blending to Moderate reddish orange [37. m.rO] with some Dark red [16. d.R] mottling or tiger striping.
*Down*.—Moderate, short, does not roll up when rubbed.
Flesh:
*Color*.—Very yellow [82. v.Y] with some Dark red [16. d.R] streaking toward the stone.
*Surface of pit cavity*.—Very deep red [14. v.deep R] broken fibers when twisted from stone.
*Amygdalin*.—Moderate.
*Juice*.—Abundant, rich.
*Texture*.—Firm, crisp, meaty.
*Fibers*.—Abundant, fine.
*Ripens*.—Fairly even, somewhat earlier toward the apex.
*Flavor*.—Classic peach flavor, acidic and sweet, typically 14 brix.
*Aroma*.—Slight.
*Eating quality*.—Very good.

STONE

Type: Clingstone.
Form: Oval.
Hilum: Broad, oval.
Base: Rounded to truncate.
Apex: Acuminate.
Sides: Equal.
Surface: Irregularly furrowed near the apex, pitted toward the base.
Ridges: Jagged.
External color: Dark reddish brown [44. d.rBr].
Pit wall color when cracked: Light brown [57. 1.Br].
Cavity surface color: Strong yellowish brown [74. s.yBr].
Average pit wall thickness: ¼" [6.4 mm.].
Average width: 1¼" [31.8 mm.].
Average length: 1¼" [31.8 mm.].
Average breadth: 13/16" [20.6 mm.].
Tendency to split: Slight.
Kernel:
*Form*.—Oval.
*Skin color*.—Deep orange yellow [69. deep OY] when first removed.
*Pellicle color*.—Dark yellowish brown [78. d.yBr].
*Vein color*.—Dark yellowish brown [78. d.yBr].
*Taste*.—Bitter.
*Viable*.—Yes.
*Average width*.—9/16" [14.3 mm.].
*Average length*.—13/16" [20.6 mm.].
*Amygdalin*.—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to Red Princess (U.S. Plant patent application Ser. No. 13/694,608 filed Dec. 13, 2012) peach by requiring about 600 chilling hours, by blooming in the mid to late season, by being self-fruitful, by having large blossoms, and by producing yellow flesh clingstone peaches that are firm, nearly full red in skin color, globose in shape, and a good tasting flavor, but is distinguished therefrom by having a larger and more vigorous tree, by having globose instead of reniform glands, and by producing fruit that is somewhat larger in size, that has a bitter kernel instead of sweet, and that matures about seventy days later.

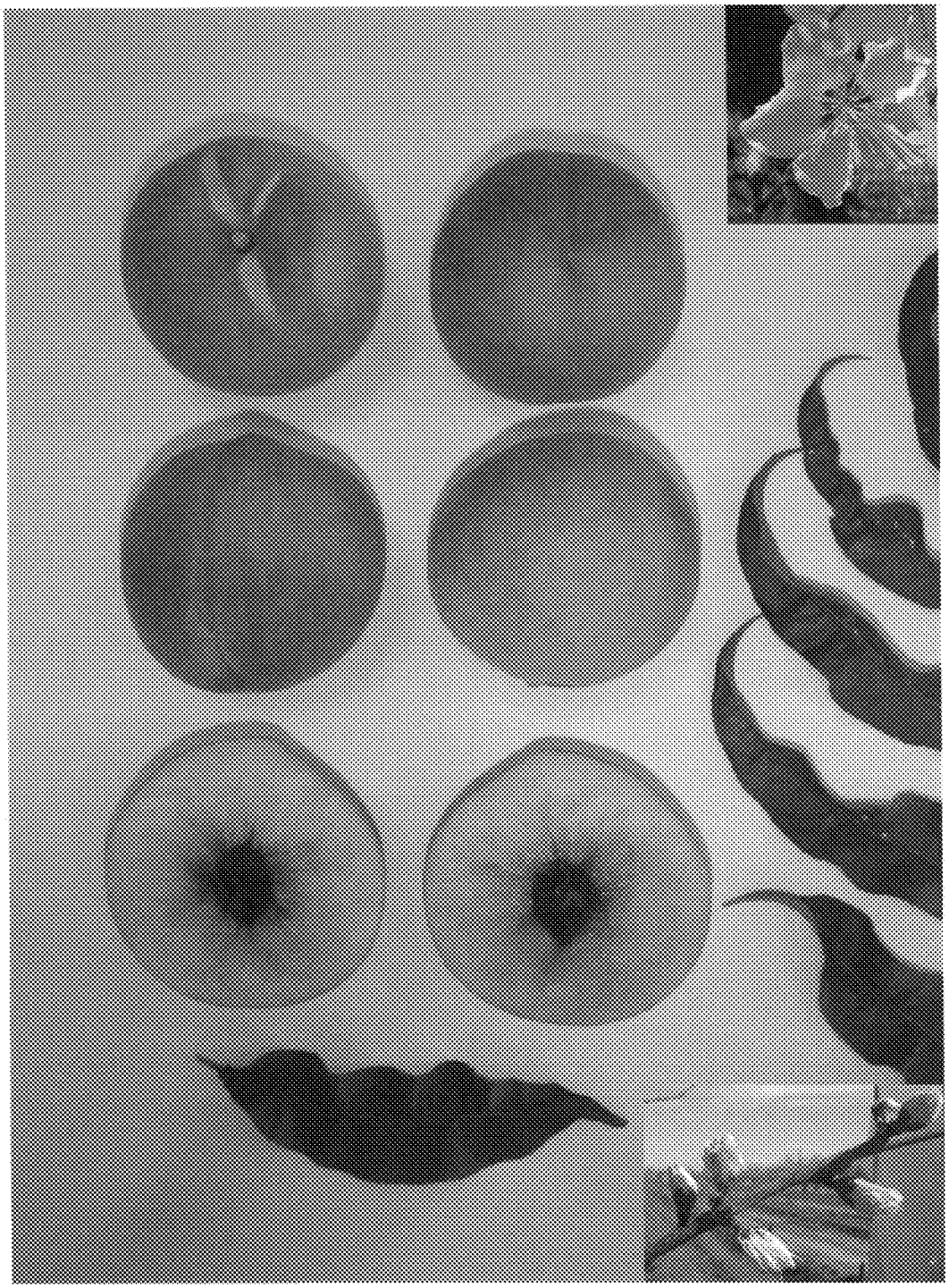

* * * * *